(12) United States Patent
Hoffmann et al.

(10) Patent No.: US 6,461,384 B1
(45) Date of Patent: *Oct. 8, 2002

(54) INTRAOCULAR LENSES

(75) Inventors: Laurent Hoffmann, Foothill Ranch, CA (US); Mark Wesley Ross, Costa Mesa, CA (US); Donald Carrol Stenger, Anaheim Hills, CA (US)

(73) Assignee: Bausch & Lomb Incorporated, Rochester, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/335,413

(22) Filed: Jun. 17, 1999

(51) Int. Cl.⁷ .................................................. A61F 2/16
(52) U.S. Cl. ..................... 623/6.51; 623/6.37; 623/6.49
(58) Field of Search ................................. 623/6.17, 6.4, 623/6.51, 6.37, 6.42, 6.49, 6.52, 6.53, 6.54, 6.47

(56) References Cited

U.S. PATENT DOCUMENTS

| | | | |
|---|---|---|---|
| 3,721,657 A | 3/1973 | Seiderman et al. | 623/6 |
| 3,792,028 A | 2/1974 | Seiderman | 623/6 |
| 3,961,379 A | 6/1976 | Highgate | 623/6 |
| 4,073,015 A | 2/1978 | Peyman et al. | 623/6 |
| 4,242,762 A | 1/1981 | Tennant | 623/6 |
| 4,249,272 A | 2/1981 | Poler | 623/6 |
| 4,254,509 A | 3/1981 | Tennant | 623/6 |
| 4,254,510 A | 3/1981 | Tennant | 623/6 |
| 4,261,065 A | 4/1981 | Tennant | 623/6 |
| 4,277,852 A | 7/1981 | Poler | 623/6 |
| 4,315,336 A | 2/1982 | Poler | 623/6 |
| 4,316,293 A | 2/1982 | Bayers | 623/6 |
| 4,361,913 A * | 12/1982 | Streck | 623/6 |
| 4,377,873 A | 3/1983 | Reichert, Jr. | 623/6 |
| 4,403,353 A | 9/1983 | Tennant | 623/6 |
| 4,424,597 A | 1/1984 | Schlegel | 623/6 |
| 4,446,581 A | 5/1984 | Blake | 623/6 |
| RE31,640 E | 8/1984 | Freeman | 623/6 |
| 4,556,998 A | 12/1985 | Siepser | 623/6 |
| 4,573,998 A | 3/1986 | Mazzocco | 623/6 |
| 4,575,374 A | 3/1986 | Anis | 623/6 |
| 4,575,878 A | 3/1986 | Dubroff | 623/6 |
| 4,585,456 A | 4/1986 | Blackmore | 623/6 |

(List continued on next page.)

FOREIGN PATENT DOCUMENTS

| | | | |
|---|---|---|---|
| AU | B-331730/84 | 8/1983 | |
| DE | 2717706 | 4/1977 | |
| DE | 3439551 A1 | 10/1984 | |
| EP | 0136807 | 8/1984 | |
| EP | 391452 B1 | 8/1984 | |
| EP | 0118985 | 9/1984 | |
| FR | 1103399 | 11/1955 | |
| GB | 2114315 A | 8/1983 | |
| GB | 2151371 A | 7/1985 | |
| WO | WO 87/01931 | 4/1987 | |
| WO | WO 96 11792 A | 4/1996 | |
| WO | WO 97/41805 * | 11/1997 | 623/6.39 |
| WO | WO 98 56315 A | 12/1998 | |

*Primary Examiner*—Paul B. Prebilic
(74) *Attorney, Agent, or Firm*—Rita D. Vacca (57) ABSTRACT

An intraocular lens including an optic portion having an outer peripheral edge and two, three or four balanced looped haptic elements for use to achieve refractive correction. Each looped haptic is formed to have greater resistance to bending in a plane generally parallel to an eye's optical axis than in a plane generally perpendicular to the eye's optical axis. The intraocular lens is designed with specific flexibility characteristics so as to exhibit less than approximately 1.0 mm axial displacement of the optic portion along the eye's optical axis under a compression force suitable to effect a 1.0 mm in diameter compression of the intraocular lens.

15 Claims, 6 Drawing Sheets

U.S. PATENT DOCUMENTS

| | | | |
|---|---|---|---|
| 4,605,409 A | 8/1986 | Kelman | 623/6 |
| 4,605,411 A | 8/1986 | Fedorov et al. | 623/6 |
| 4,615,702 A | 10/1986 | Koziol et al. | 623/6 |
| 4,629,460 A | 12/1986 | Dyer | 623/6 |
| 4,629,462 A | 12/1986 | Feaster | 623/6 |
| 4,634,441 A | 1/1987 | Clayman et al. | 623/6 |
| 4,642,113 A | 2/1987 | Dubroff | 623/6 |
| 4,642,116 A | 2/1987 | Clayman et al. | 623/6 |
| 4,664,666 A | 5/1987 | Barrett | 623/6 |
| 4,673,406 A | 6/1987 | Schlegel | 623/6 |
| 4,676,791 A | 6/1987 | LeMaster et al. | 623/6 |
| 4,676,792 A | 6/1987 | Praeger | 623/6 |
| 4,687,485 A | 8/1987 | Lim et al. | 623/6 |
| RE32,525 E | 10/1987 | Pannu | 623/6 |
| 4,704,123 A | 11/1987 | Smith | |
| 4,718,904 A | 1/1988 | Thornton | 623/6 |
| 4,718,906 A | 1/1988 | Mackool | 623/6 |
| 4,725,277 A | 2/1988 | Bissonette | 623/6 |
| 4,734,095 A | 3/1988 | Siepser | 623/6 |
| 4,769,035 A | 9/1988 | Kelman | 623/6 |
| 4,781,717 A | 11/1988 | Gendahl | 623/6 |
| 4,787,904 A | 11/1988 | Severin et al. | 623/6 |
| 4,816,030 A * | 3/1989 | Robinson | 623/6 |
| RE33,039 E | 8/1989 | Arnott | 623/6 |
| 4,863,466 A | 9/1989 | Schlegel | 623/6 |
| 4,932,970 A | 6/1990 | Portney | 623/6 |
| 4,936,850 A | 6/1990 | Barrett | 623/6 |
| 4,997,442 A | 3/1991 | Barrett | 623/6 |
| 5,002,568 A | 3/1991 | Katzen | 623/6 |
| 5,047,502 A | 9/1991 | Dubroff | 623/6 |
| 5,066,301 A | 11/1991 | Wiley | 623/6 |
| 5,071,432 A | 12/1991 | Baikoff | 623/6 |
| 5,078,742 A | 1/1992 | Dahan | 623/6 |
| 5,092,880 A | 3/1992 | Ohmi | 623/6 |
| 5,100,226 A | 3/1992 | Freeman | 623/6 |
| 5,108,429 A | 4/1992 | Wiley | 623/6 |
| 5,133,749 A | 7/1992 | Nordan | 623/6 |
| 5,147,395 A | 9/1992 | Willis | 623/6 |
| 5,171,266 A | 12/1992 | Wiley et al. | 623/6 |
| 5,196,026 A | 3/1993 | Barrett et al. | 623/6 |
| 5,197,981 A | 3/1993 | Southard | 623/6 |
| 5,203,788 A | 4/1993 | Wiley | 623/6 |
| 5,203,790 A | 4/1993 | McDonald | 623/6 |
| 5,211,662 A | 5/1993 | Barrett et al. | 623/6 |
| 5,217,491 A | 6/1993 | Vanderbilt | 623/6 |
| 5,222,981 A | 6/1993 | Werblin | 623/6 |
| 5,258,025 A | 11/1993 | Fedorov et al. | 623/6 |
| 5,336,261 A | 8/1994 | Barrett et al. | 623/6 |
| 5,476,514 A | 12/1995 | Cummings | 623/6 |
| 5,578,080 A * | 11/1996 | McDonald | 623/6 |
| 5,713,958 A * | 2/1998 | Weiser | 623/6 |
| 5,716,403 A | 2/1998 | Tran et al. | 623/6 |
| 6,117,171 A * | 9/2000 | Skottum | 623/6.37 |
| 6,179,870 B1 * | 1/2001 | Sourdille et al. | 623/6.39 |

* cited by examiner figure 6 figure 7 figure 8

INTRAOCULAR LENSES

FIELD OF THE INVENTION

The present invention relates to intraocular lenses (IOLs) and a method for making and using the same. More particularly, the present invention relates to IOLs designed primarily for refractive correction in phakic eyes where the eye's natural lens remains intact. IOLs made in accordance with the present invention may also be used in aphakic eyes where a diseased natural lens is surgically removed, such as in the case of cataracts.

BACKGROUND OF THE INVENTION

Visual acuity deficiencies such as myopia (nearsightedness), hyperopia (farsightedness) and presbyopia (age-related farsightedness) are typically corrected with use of refractive lenses such as spectacles or contact lenses. Although these types of lenses are effective in correcting a wearer's eyesight, many wearers consider the lenses inconvenient. The lenses must be located, worn at certain times, removed periodically and may be lost or misplaced. The lenses may also be dangerous or cumbersome if the wearer participates in athletic activities or suffers an impact in an area near the eyes.

The use of surgically implanted IOLs as a permanent form of refractive correction in phakic eyes has been gaining in popularity. IOL implants have been used for many years in aphakic eyes as replacements for diseased natural crystalline lenses that have been surgically removed from the eyes. Many different IOL designs have been developed over past years and proven successful for use in aphakic eyes. Successful IOL designs to date primarily include an optic portion with supports therefor, called haptics, connected to and surrounding at least part of the optic portion. The haptic portions of an IOL are designed to support the optic portion of the IOL in the lens capsule, anterior chamber or posterior chamber of an eye.

Commercially successful IOLs have been made from a variety of biocompatible materials, ranging from more rigid materials such as polymethylmethacrylate (PMMA) to softer, more flexible materials capable of being folded or compressed such as silicones, certain acrylics, and hydrogels. Haptic portions of the IOLs have been formed separately from the optic portion and later connected thereto through processes such as heat, physical staking and/or chemical bonding. Haptics have also been formed as an integral part of the optic portion in what is commonly referred to as "single-piece" IOLs.

Softer, more flexible IOLs have gained in popularity in more recent years due to their ability to be compressed, folded, rolled or otherwise deformed. Such softer IOLs may be deformed prior to insertion thereof through an incision in the cornea of an eye. Following insertion of the IOL in an eye, the IOL returns to its original pre-deformed shape due to the memory characteristics of the soft material. Softer, more flexible IOLs as just described may be implanted into an eye through an incision that is much smaller, i.e., 2.8 to 3.2 mm, than that necessary for more rigid IOLs, i.e., 4.8 to 6.0 mm. A larger incision is necessary for more rigid IOLs because the lens must be inserted through an incision in the cornea slightly larger than the diameter of the inflexible IOL optic portion. Accordingly, more rigid IOLs have become less popular in the market since larger incisions have been found to be associated with an increased incidence of postoperative complications, such as induced astigmatism.

After IOL implantation, both softer and more rigid IOLs are subject to compressive forces exerted on the outer edges thereof, which typically occur when an individual squints or rubs the eye. These compressive forces may result in decentration of the IOL and distortion of the visual image. Compressive forces exerted on an IOL also tend to cause axial displacement of the IOL along the optical axis of an eye. Movement of an IOL along the optical axis of an eye has the potential in anterior chamber applications to cause the IOL to contact and damage the delicate corneal endothelial cell layer of the eye. Such potential damage to the delicate corneal endothelial cell layer is due in part to the design of anterior chamber IOLs that are vaulted to prevent interference or damage to the iris of an eye. Also, IOLs of current designs, whether vaulted or unvaulted, or formed of either softer or more rigid materials, tend to deflect along the optical axis of an eye when the haptics are compressed. IOL manufacturers provide a wide range of IOL sizes to more precisely fit IOLs to each particular patient's eye size. Providing a wide range of IOL sizes is an attempt to minimize the potential for axial displacement of the IOL along the optical axis of an eye.

Because of the noted shortcomings of current IOL designs, there is a need for IOLs designed to minimize axial displacement of the IOL optic portion along the optical axis of the eye when compressive forces are exerted against the outer edges thereof. By lessening an IOLs movement along the optical axis of an eye, more certain refractive correction may be achieved and the risk of corneal endothelial cell layer damage may be reduced.

SUMMARY OF THE INVENTION

An intraocular lens (IOL) made in accordance with the present invention has an optic portion with an outer peripheral edge and two, three or four looped haptic elements for supporting the optic portion in a patient's eye. A lens having two looped haptic elements is balanced by having a looped haptic element formed or attached on two opposed edges of the optic portion. A lens having three looped haptic elements is balanced by having a set of two looped haptic elements formed or attached on one edge of the optic and the third looped haptic element formed or attached on an opposite edge of the optic. A lens having four looped haptic elements is balanced by having a set of two looped haptic elements formed or attached on one edge of the optic and a set of two looped haptic elements formed or attached on an opposite edge of the optic. Each looped haptic element has an inner edge portion, an outer edge portion and generally two attachment portions that permanently connect the looped haptic elements to the outer peripheral edge of the optic portion. In the case of lenses having three or four looped haptic elements, a set of two looped haptic elements may have three attachment portions rather than four. In such a case, one of the three attachment portions is common to each of the two looped haptic elements in the set. Each looped haptic element also includes a flexible central portion located adjacent to each of the two attachment portions and a contact plate located between the two flexible central portions. The contact plate is designed to engage an inner surface of a patient's eye. The two flexible central portions that extend between the contact plate and the attachment portions allow the lens to adjust to pressures exerted on the lens within the eye. Additionally, within these flexible central portions, each looped haptic element is designed to have greater resistance to bending in a plane generally parallel to the optical axis of an eye than in a plane generally perpendicular to the optical axis of an eye. By providing looped haptic elements with this type of flexibility characteristic, the present IOL fits eyes of varying sizes. The flexibility characteristic of the subject looped haptic elements relative to the optic portion also eliminates unacceptable axial displacement of the optic portion along the optical axis when compressive forces are exerted against the looped haptic elements of the IOL.

Accordingly, it is an object of the present invention to provide intraocular lenses for use in phakic eyes.

Another object of the present invention is to provide intraocular lenses for use in phakic eyes, which fit a variety of eye sizes.

Another object of the present invention is to provide intraocular lenses for use in phakic eyes, which minimize axial displacement of the optic portions of the lenses along the optical axis of the eyes.

Another object of the present invention is to provide intraocular lenses for use in phakic eyes, which minimize damage to tissues in the interior of the eyes.

Still another object of the present invention is to provide intraocular lenses, which are resistant to decentration within the eyes.

These and other objectives and advantages of the present invention, some of which are specifically described and others that are not, will become apparent from the detailed description, drawings and claims that follow, wherein like features are designated by like numerals.

DETAILED DESCRIPTION OF THE INVENTION

Figure 1:
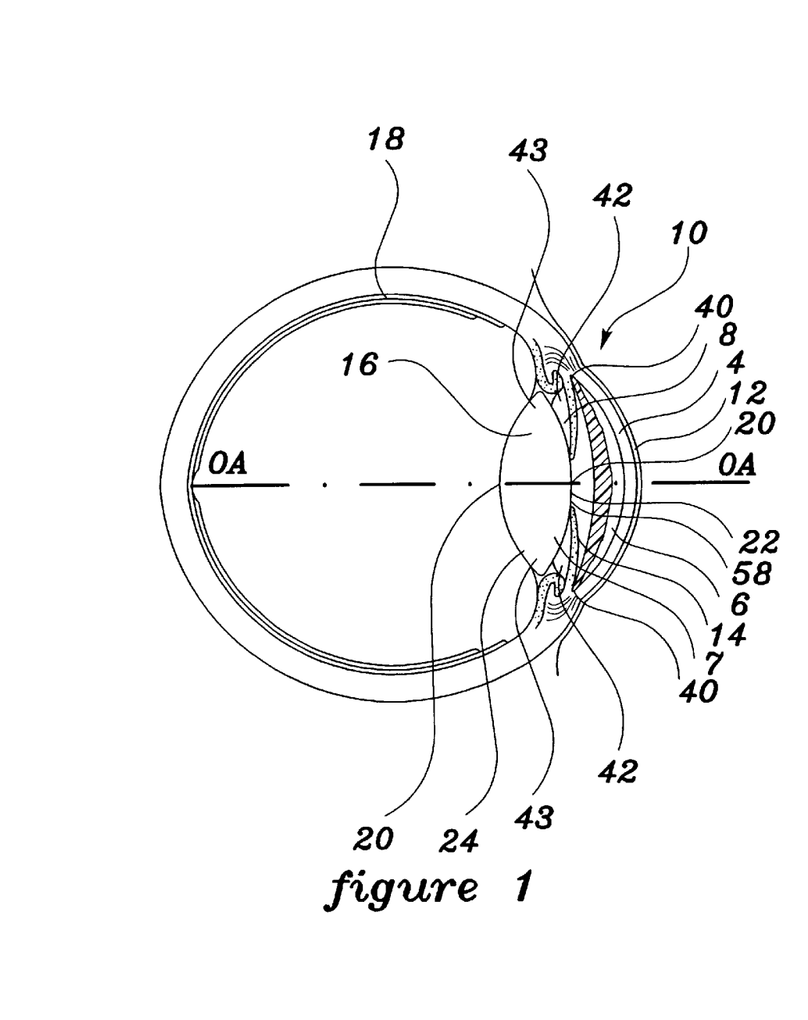
FIG. 1 is a schematic representation of the interior of a human eye including a natural lens and a refractive IOL implanted in the anterior chamber of the eye.

FIG. 1 illustrates a simplified diagram of an eye 10 showing landmark structures relevant to the implantation of an intraocular lens of the present invention. Eye 10 includes an optically clear cornea 12 and an iris 14. A natural crystalline lens 16 and a retina 18 are located behind the iris 14 of eye 10. Eye 10 also includes anterior chamber 6 located in front of iris 14 and a posterior chamber 8 located between iris 14 and natural lens 16. IOLs of the present invention are preferably implanted in anterior chamber 6 to correct refractive errors while healthy natural lens 16 remains in place (phakic application). IOLs of the present invention may also be implanted in posterior chamber 8 or lens capsule 7 for use in aphakic eyes. When used in aphakic eyes, IOLs serve as replacements for surgically removed diseased natural lenses 16, such as for example following cataract surgeries. Eye 10 also includes an optical axis OA—OA that is an imaginary line that passes through the optical center 20 of anterior surface 22 and posterior surface 24 of lens 16. Optical axis OA—OA in the human eye 10 is generally perpendicular to a portion of cornea 12, natural lens 16 and retina 18.

The IOL of the present invention, as illustrated in FIGS. 2 through 14 but best illustrated in FIGS. 2, 9, 11 and 13, is identified generally by reference numeral 26. IOL 26 has an optic portion 28 with an outer peripheral edge 30. IOL 26 is designed for implantation preferably in anterior chamber 6 of a patient's eye 10 and is preferably vaulted. For anterior chamber 6 applications, a vault of approximately 1.0 to 2.0 mm but preferably 1.6 to 1.7 mm measuring from the plane of outer peripheral edge 30 of optic portion 28 to the plane of contact plates 38, described in detail below, is generally suitable. However as mentioned above, IOL 26 may likewise be implanted in posterior chamber 8 or in the case of an aphakic eye, in lens capsule 7 in which case IOL 26 need not be vaulted. Preferably integrally formed on peripheral edge 30 of optic portion 28 are two, three or four looped haptic elements 32, each having an inner edge portion 34 and an outer edge portion 36. Looped haptic elements 32 are preferably integrally formed with and permanently connected to outer peripheral edge 30 of optic portion 28 by attachment portions 33. Alternatively however, haptic elements 32 may be attached to optic portion 28 by staking, chemical polymerization or other methods known to those skilled in the art. Each looped haptic element 32 also includes a broadened contact plate 38 designed to preferably engage inner surfaces 40 in anterior chamber 6. However, contact plate 38 is also suitable to engage inner surfaces 42 in posterior chamber 8 or inner surfaces 43 in lens capsule 7 of eye 10.

In accordance with the present invention, looped haptic elements 32 are designed so that when IOL 26 is implanted in a patient's eye 10 and held in place through compressive forces exerted by inner surfaces 40, 42 or 43 on contact plates 38 of looped haptic elements 32, looped haptic elements 32 flex so that contact plates 38 do not slide along surfaces 40, 42 or 43 in the eye 10. Accordingly, looped haptic elements 32 are designed to flex in a plane generally parallel to that of optic portion 28 of IOL 26 and generally perpendicular to that of optical axis OA—OA of eye 10. By designing this type of flexibility characteristic into looped haptic elements 32, IOL 26 may be manufactured in one or a few standard sizes and be a suitable fit for most sizes of patients' eyes 10. The flexibility characteristic of looped haptic elements 32 also minimizes axial displacement of optic portion 28 in a direction along optical axis OA—OA of eye 10. Compressive forces of differing magnitudes within the range of approximately 0.1 to 5 mN exerted against contact plates 38 of looped haptic elements 32 to effect approximately an overall 1.0 mm in diameter compression of IOL 26, such as that caused by differing eye sizes, results in less than approximately 1.0 mm, but more preferably less than approximately 0.5 mm and most preferably less than approximately 0.3 mm axial displacement of optic portion 28 along optical axis OA—OA in an eye 10. Under like compressive forces, IOLs known in the art result in greater than 1.0 mm axial displacement of the optic portion along the optical axis in the eye, which may damage delicate tissues therein. The unique design of IOL 26 achieves significantly minimized axial displacement of optic portion 28. The IOL 26 of the present invention with its minimized axial displacement of optic portion 28 protects the corneal endothelium cell layer 4 of eye 10 from damage when a wide range of compressive forces, potentially even greater than those described above, are applied to eye 10.

Figure 2:
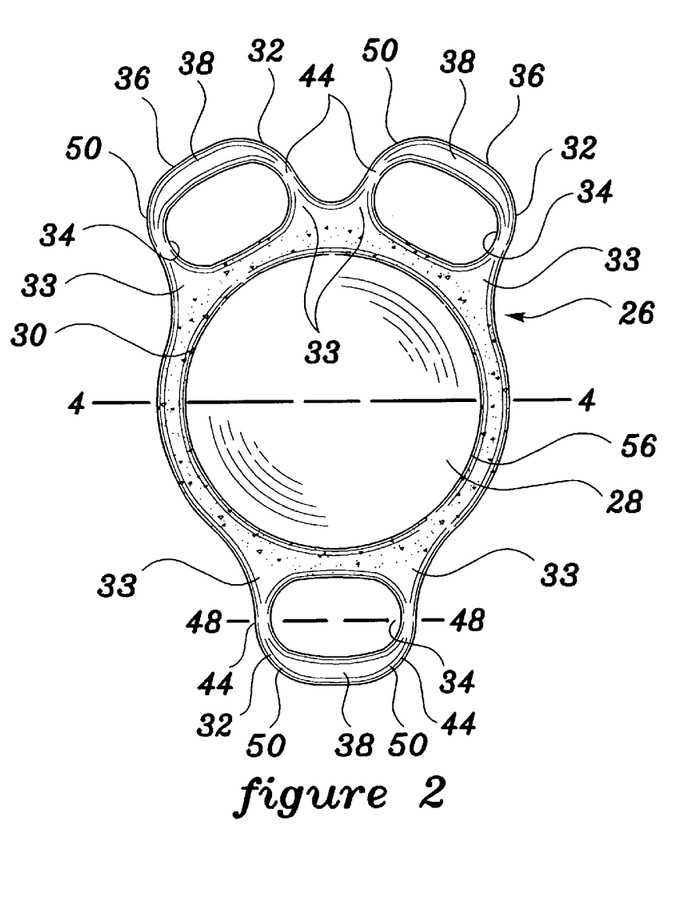
FIG. 2 is a plan view of an IOL with three looped haptics made in accordance with the present invention.
Figures 3, 4, 5:
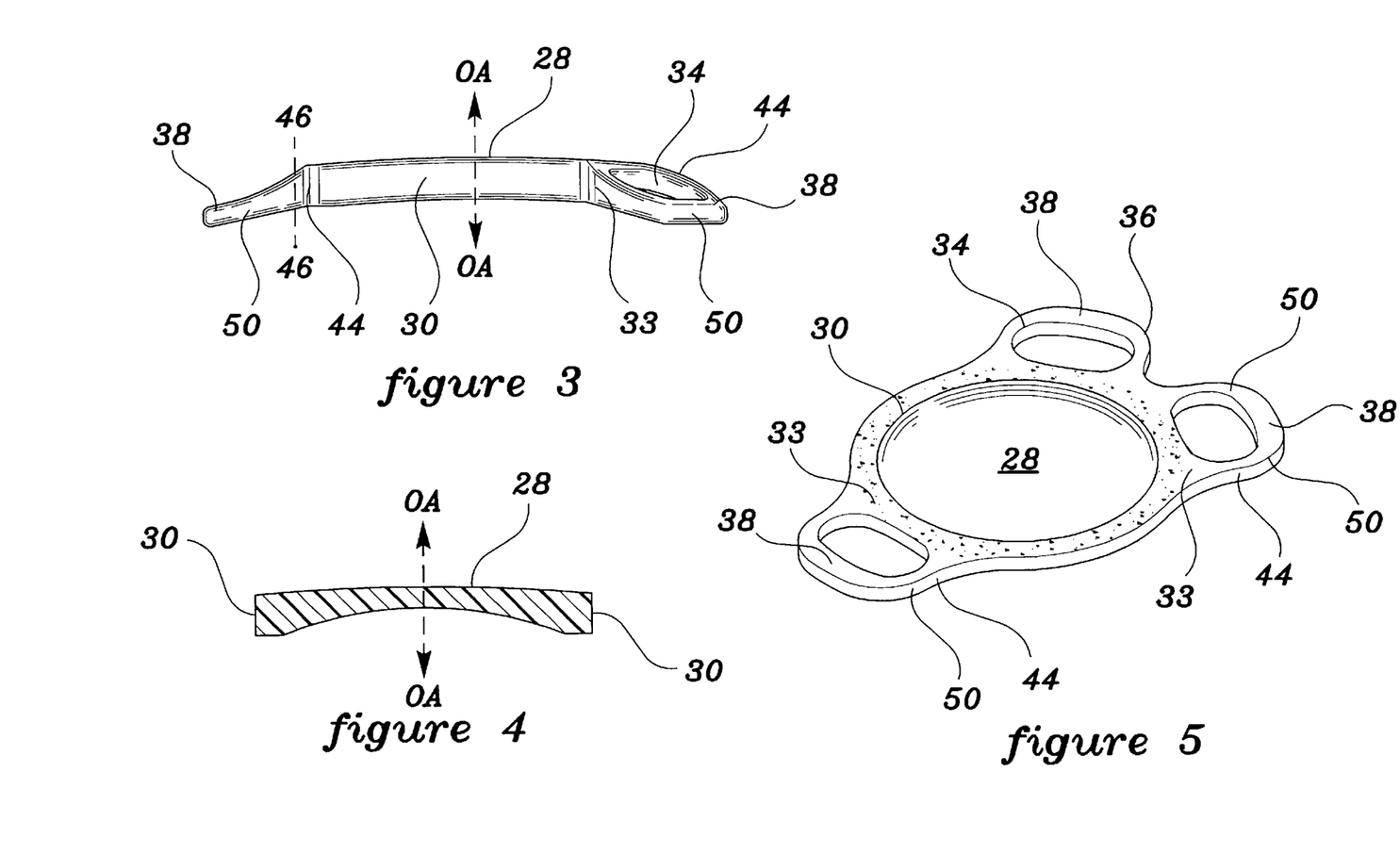
FIG. 3 is a side view of the IOL of FIG. 2.
FIG. 4 is a cross sectional view of the IOL of FIG. 2 taken along line 4—4.
FIG. 5 is a perspective view of the IOL of FIG. 2.
Figure 6:
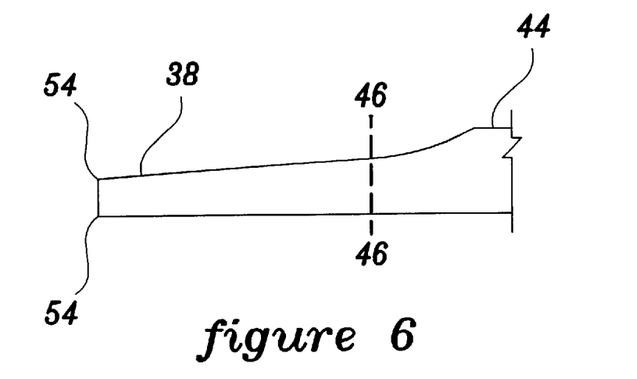
FIG. 6 is a side view of the looped haptic element of FIG. 3 with sharper edges.
Figure 7:
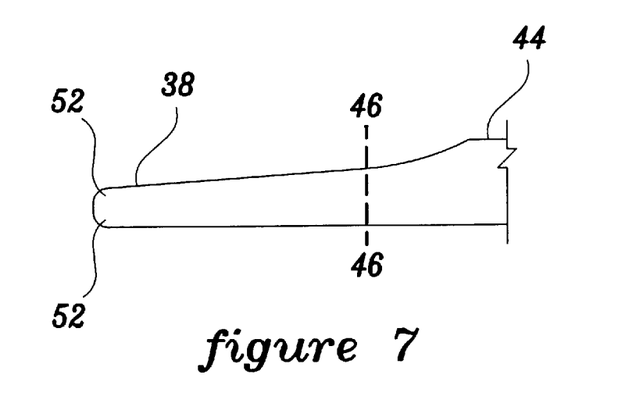
FIG. 7 is a side view of the looped haptic element of FIG. 3 with rounded edges.

The flexibility characteristic of looped haptic elements 32 of IOL 26 as described above is achieved through the unique design thereof. As best illustrated in FIGS. 2, 9,11 and 13, and most particularly in FIG. 11, IOL 26 has looped haptic elements 32 formed with angled, arched or bowed flexible central portions 44 adjacent to attachment portions 33 permanently connected to outer peripheral edge 30 of optic portion 28. The angled, arched or bowed flexible central portions 44 are essential in imparting the necessary flexibility to the IOLs of the present invention. As best illustrated in FIGS. 3,10, 12 and 14, flexible central portions 44 have a dimension in plane 46—46, generally parallel to optical axis OA—OA, equal to or greater than the same in plane 48—48 generally perpendicular to optical axis OA—OA as depicted in FIG. 2. Transition portions 50, of significantly decreasing size in dimension in plane 46—46 extend from flexible central portions 44 to broadened contact plate 38. Contact plate 38 is relatively flat with either rounded edges 52 as depicted in FIG. 7 to provide a smoother fit with inner surfaces 40, 42 or 43, or more defined, sharper edges 54 as depicted in FIG. 6 to provide a barrier to prevent cellular migration and growth upon implantation in lens capsule 7. The relatively thin or flat contact plate 38 also minimizes iris 14 contact by virtue of its overall angled, arched or bowed cross section as illustrated in FIGS. 6 through 8.

The subject IOL 26 is preferably manufactured to have an optic portion 28 approximately 4.5 to 9.0 mm, but preferably approximately 5.0 to 6.0 mm and most preferably 5.5 mm in diameter and approximately 0.15 mm to 1.0 mm, but preferably approximately 0.6 to 0.8 mm and most preferably 0.7 mm in thickness at peripheral edge 30. Looped haptic elements 32 extend from the optic portion 28 of IOL 26 in a generally rounded or oval configuration and will increase or decrease in overall length depending upon the size of lens desired and the diameter of optic portion 28. As the diameter of optic portion 28 increases, the overall length of looped haptic elements 32 may be decreased. Likewise, as the diameter of optic portion 28 decreases, the overall length of looped haptic elements 32 may be increased. However, as customary, the overall length of the looped haptic elements 32 are varied to achieve desired IOL 26 sizes rather than varying the sizes of optic portions 28. In general, looped haptic elements 32 are formed to be approximately 2.6 to 6.0 mm, but preferably approximately 3.4 to 5.0 mm and most preferably approximately 4.2 mm in length measuring from a point of equal distance between common attachment portions 33 on peripheral edge 30, to the center of contact plate 38. Looped haptic elements 32 are preferred to have a generally rounded or oval configuration as illustrated in FIGS. 2, 9, 11 and 13 to allow radial deflection under compressive forces. For purposes of the present invention, the generally rounded or oval shape of looped haptic element 32, i.e., the beam curve shape, relative to the width to thickness ratio, i.e., the aspect ratio, of looped haptic element 32 as described herein is critical to achieve suitable function. Flexible central portion 44 of looped haptic element 32 is approximately 0.5 to 2.5 mm, but preferably approximately 1.0 to 2.0 mm and most preferably 1.6 mm in length; approximately 0.2 to 1.0 mm, but preferably approximately 0.3 to 0.7 mm and most preferably approximately 0.46 mm in thickness in plane 46—46 and approximately 0.2 to 0.7 mm, but preferably approximately 0.3 to 0.6 and most preferably approximately 0.43 mm in width in plane 48—48. Transition portions 50 are approximately 0.4 to 1.1 mm, but preferably approximately 0.5 to 1.0 mm and most preferably approximately 0.8 mm in length. Contact plate 38 is approximately 0.8 to 2.5 mm, but preferably approximately 1.0 to 2.2 mm and most preferably approximately 1.8 mm in length, approximately 0.05 to 0.5 mm, but preferably approximately 0.1 to 0.4 mm and most preferably approximately 0.3 mm in thickness and approximately 0.6 to 1.5 mm, but preferably approximately 0.8 to 1.2 mm and most preferably approximately 1.0 mm in width.

As provided through the dimensions of IOL 26 above, looped haptic elements 32 gradually change from being relatively thin in plane 46—46 at outer edge portion 36 to being relatively thick at attachment portions 33 and optic portion 28, with flexible central portions 44 preferably exhibiting a thicker dimension in plane 46—46 than that of the width in plane 48—48. Looped haptic elements 32 of the subject design tend to deflect into closer proximity with outer peripheral edge 30 when a compression force is exerted against contact plates 38 with minimal axial displacement along optical axis OA—OA. When IOL 26 is used as a refractive lens, a stable, reliable refractive correction is provided.

Figure 8:
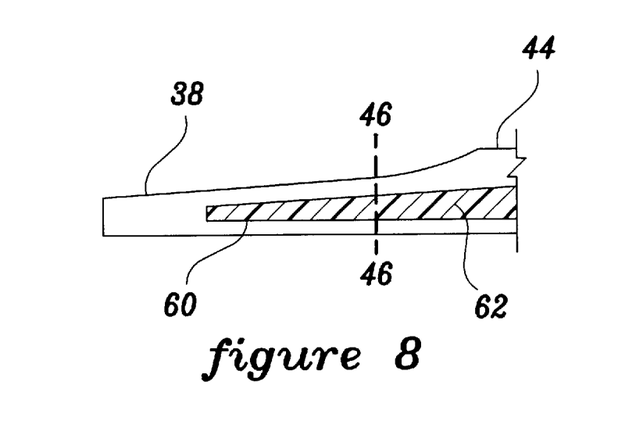
FIG. 8 is a side cross sectional view of the looped haptic element of FIG. 6 with a stiffening element.
Figure 9:
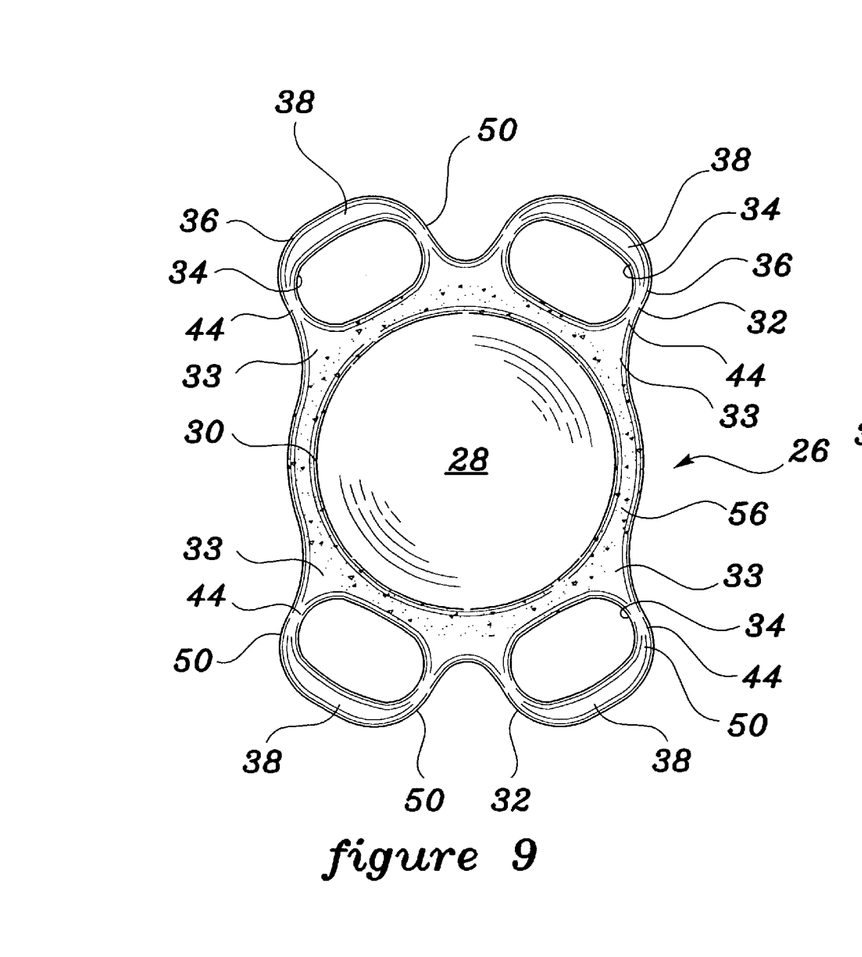
FIG. 9 is a plan view of an IOL with four looped haptics made in accordance with the present invention.
Figure 10:
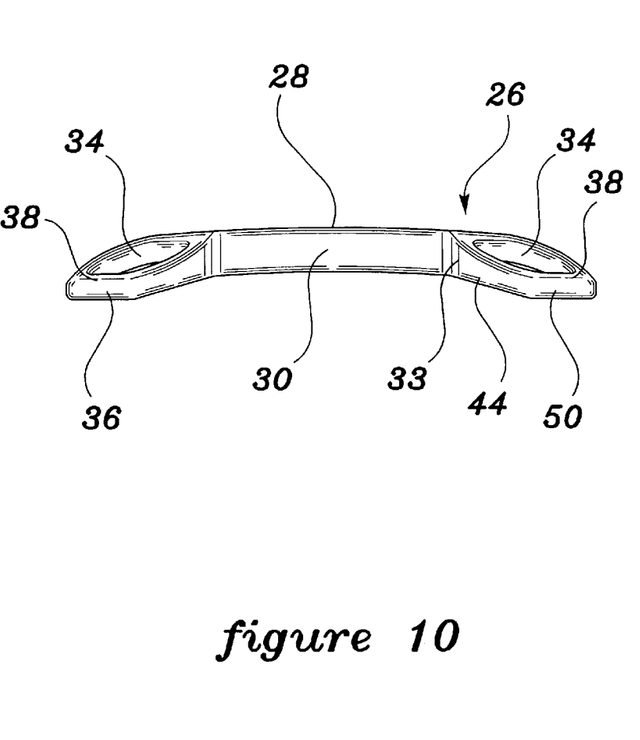
FIG. 10 is a side view of the IOL of FIG. 9.
Figure 11:
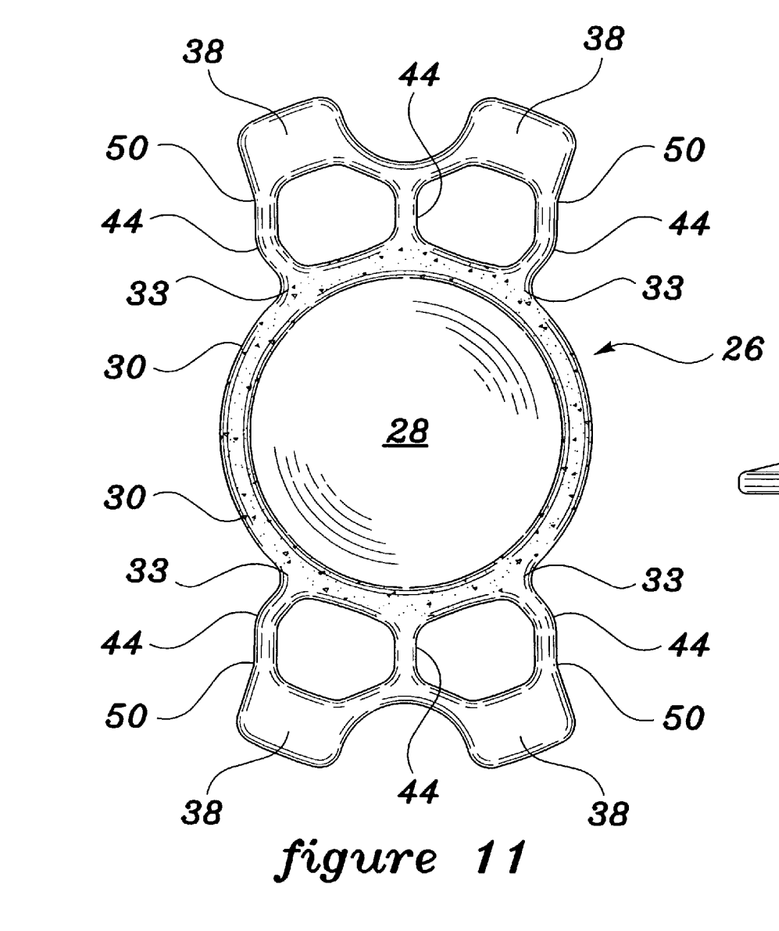
FIG. 11 is a plan view of an IOL with four looped haptics made in accordance with the present invention.
Figure 12:
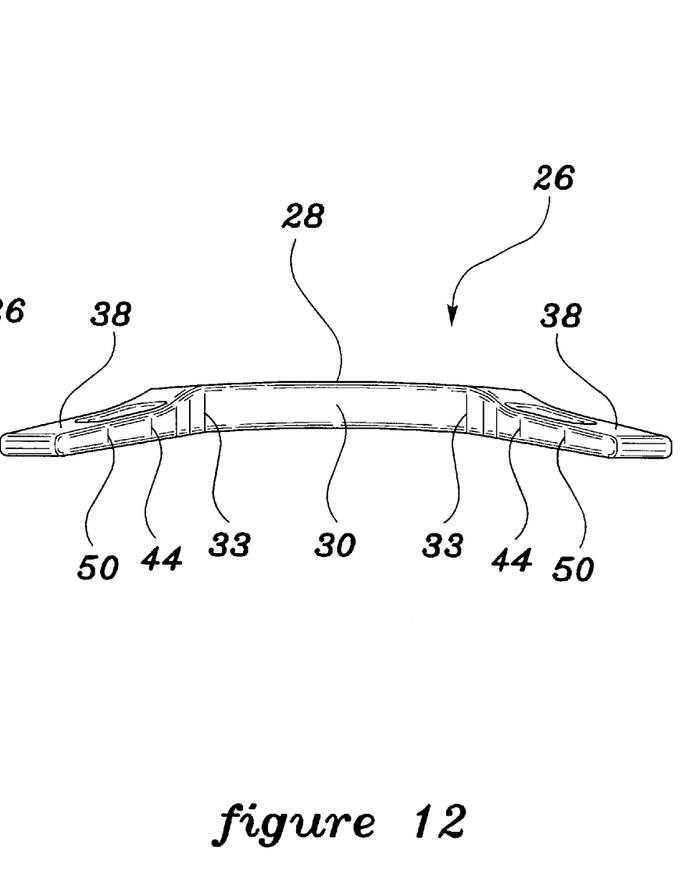
FIG. 12 is a side view of the IOL of FIG. 11.
Figure 13:
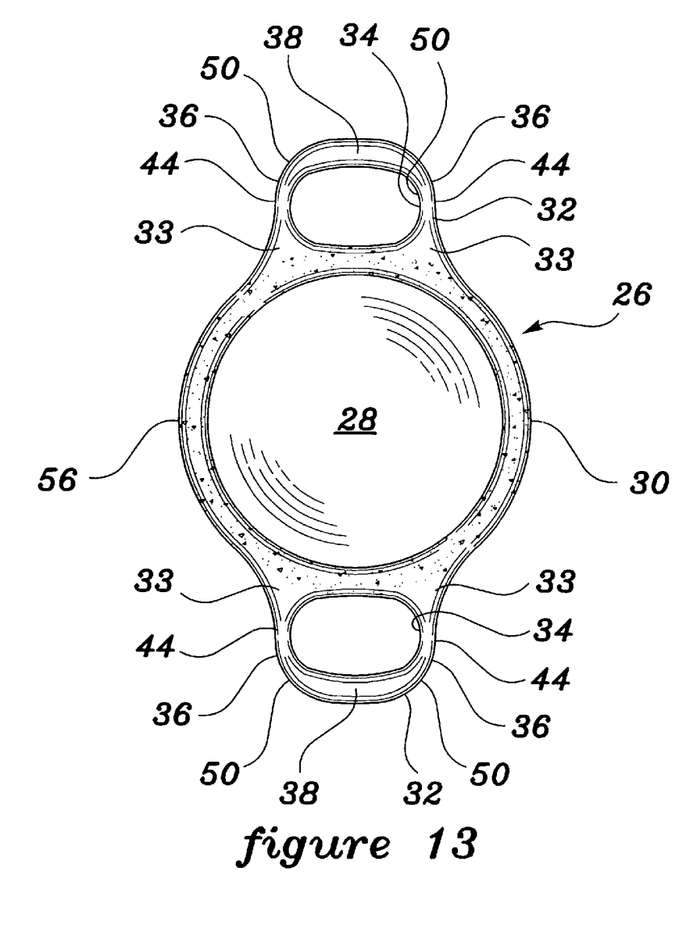
FIG. 13 is a plan view of an IOL with two looped haptics made in accordance with the present invention.
Figure 14:
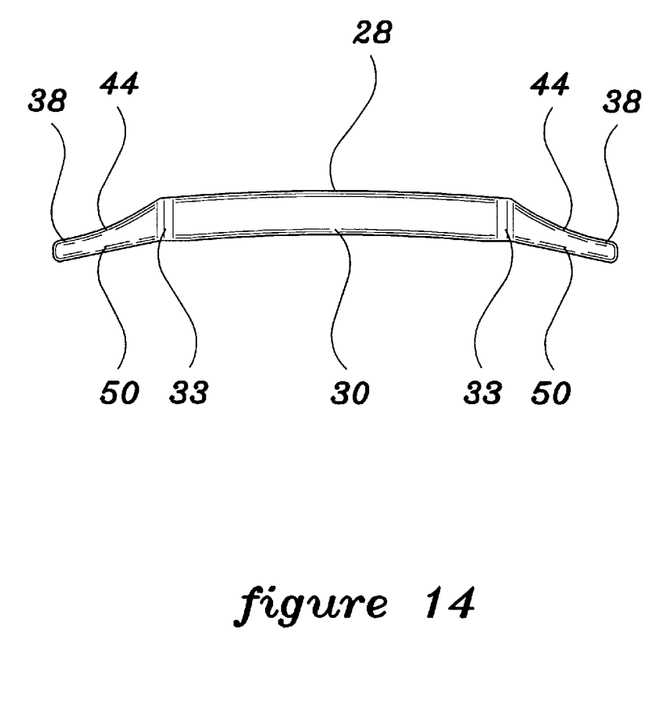
FIG. 14 is a side view of the IOL of FIG. 13.

The desired flexibility characteristic of looped haptic elements 32 of IOL 26 may likewise be achieved or enhanced by incorporating a stiffening element 60, in the shape of a ribbon, in one or more looped haptic elements 32, as illustrated in FIG. 8. Stiffening element 60 may be positioned in looped haptic element 32 so that flat face 62 is oriented parallel to the dimension 46—46. Stiffening element 60 functions in a manner similar to that of an I-beam in construction to prevent axial displacement along optical axis OA—OA when compressive force is applied to contact plates 38.

Stiffening element 60 is formed of a less flexible material than that of IOL 26. Suitable materials for stiffening element 60 include but are not limited to polyimides, polyolefins, high-density polyethylenes, polyesters, nylons, metals or any biocompatible material with suitable stiffening characteristics. Stiffening element 60 may be used in conjunction with looped haptic elements 32 described above or in cases where a thinner haptic design is desired while still achieving the desired flexibility characteristics.

Suitable materials for the production of the subject IOL 26 include but are not limited to foldable or compressible materials, such as silicone polymers, hydrocarbon and fluorocarbon polymers, hydrogels, soft acrylic polymers, polyesters, polyamides, polyurethane, silicone polymers with hydrophilic monomer units, fluorine-containing polysiloxane elastomers and combinations thereof. The preferred material for the production of IOL 26 of the present invention is a hydrogel made from 2-hydroxyethyl methacrylate (HEMA) and 6-hydroxyhexyl methacrylate (HOHEXMA), i.e., poly(HEMA-co-HOHEXMA). Poly(HEMA-co-HOHEXMA) is the preferred material for the manufacture of IOL 26 due to its equilibrium water content of approximately 18 percent by weight, and high refractive index of approximately 1.474, which is greater than that of the aqueous humor of the eye, i.e., 1.33. A high refractive index is a desirable feature in the production of IOLs to impart high optical power with a minimum of optic thickness. By using a material with a high refractive index, visual acuity deficiencies may be corrected using a thinner IOL. A thin IOL, such as that of IOL 26, is particularly desirable in phakic applications to minimize potentially harmful contact between IOL 26 and iris 14 and corneal endothelium 4. Poly(HEMA-co-HOHEXMA) is also a desirable material in the production of IOLs 26 due to its mechanical strength, which is suitable to withstand considerable physical manipulation. Poly(HEMA-co-HOHEXMA) also has desirable memory properties suitable for IOL use. IOLs manufactured from a material possessing good memory properties such as those of poly(HEMA-co-HOHEXMA) unfold in a more controlled manner in an eye, rather than explosively, to its predetermined shape. The unique design of the subject IOL 26 with looped haptic elements 32 manufactured from a material having good memory properties also provides improved control of haptic unfolding upon insertion thereof in eye 10. Explosive unfolding of IOLs is undesirable due to potential damage to delicate tissues within the eye. Poly (HEMA-co-HOHEXMA) also has dimensional stability in the eye, which is desirable.

Although the teachings of the present invention are preferably applied to soft or foldable IOLs formed of a foldable or compressible material, the same may also be applied to harder, less flexible lenses formed of a relatively rigid material such as polymethylmethacrylate (PMMA) having flexible haptics formed either of the same or a different material.

Optic portion 28 of IOL 26 can be a positive powered lens from 0 to approximately +40 diopters or a negative powered lens from 0 to approximately −30 diopters. Optic portion 28 may be biconvex, plano-convex, plano-concave, biconcave or concave-convex (meniscus), depending upon the power required to achieve the appropriate central and peripheral thickness for efficient handling.

Optic portion 28 of the subject IOL 26 may optionally be formed with a glare reduction zone 56 of approximately 0.25 to 2.00 mm but more preferably approximately 0.3 to 0.6 mm and most preferably 0.5 mm in width adjacent outer peripheral edge 30 for reducing glare when outer peripheral edge 30 of IOL 26 is struck by light entering eye 10 during high light or at other times when pupil 58 is dilated. Glare reduction zone 56 is typically fabricated of the same material as optic portion 28, but may be opaque, colored or patterned in a conventional manner to block or diffuse light in plane with optical axis OA—OA.

Subject IOL 26 may be molded or preferably manufactured by first producing discs from a material of choice as described in U.S. Pat. Nos. 5,217,491 and 5,326,506 each incorporated herein in its entirety by reference. If discs are produced, IOL 26 is then be machined from the material discs in a conventional manner. Once machined or molded, IOL 26 may be polished, cleaned, sterilized and packaged by a conventional method known to those skilled in the art.

Subject IOL 26 is used in eye 10 by creating an incision in cornea 12, inserting IOL 26 in either anterior chamber 6 or posterior chamber 8 and closing the incision. Alternatively, IOL 26 may be used in eye 10 by creating an incision in cornea 12 and capsule 7, removing natural lens 16, inserting IOL 26 in capsule 7 and closing the incision.

IOL 26 of the present invention provides for a refractive lens suitable for use in lens capsule 7 or posterior chamber 8, but most preferably for use in anterior chamber 6 of eye 10. IOL 26 has looped haptic elements 32 with flexibility characteristics that minimize axial displacement along optical axis OA—OA of eye 10 thereby preventing decentration of IOL 26, distortion of vision and damage to corneal endothelium 4. IOL 26, having the flexibility characteristics described herein, is also commercially desirable because one or a few lens sizes suitably fit eyes 10 of most sizes. By providing a lens suitable for use as a "universal" lens, such as that of the present invention, clinical risks to patients due to improperly sized lenses are minimized. Such clinical risks minimized include pupil ovalization, corneal endothelium damage and poor fixation. Likewise, manufacturers' need to produce IOLs of many sizes to fit eyes of many sizes is eliminated, thus reducing production and inventory costs associated therewith. Ophthalmologists also benefit from the subject IOL 26 in that time is saved by eliminating the need to determine each patient's eye size and costs associated with maintaining large inventories of varying sized lenses.

While there is shown and described herein certain specific embodiments of the present invention, it will be manifest to those skilled in the art that various modifications may be made without departing from the spirit and scope of the underlying inventive concept and that the same is not limited to the particular forms herein shown and described except insofar as indicated by the scope of the appended claims.

We claim:

1. An intraocular lens to be implanted within an eye generally perpendicular to the eye's optical axis comprising:
   an outer peripheral edge defining an optic portion,
   two, three or four looped haptic elements each of non-uniform cross-section, each of non-uniform thickness as measured between an anterior surface for facing the cornea of the eye and a posterior surface for facing the retina of the eye of said haptic element and each permanently connected to said outer peripheral edge by two or more attachment portions of greatest haptic element thickness measured from the anterior to the posterior surface and becoming increasingly thin moving outwardly in a direction away from the optic portion, and
   each haptic element having flexible central portions flexible in a plane perpendicular to said eye's optical axis, unitarily formed with said attachment portions opposite said outer peripheral edge and dimensioned be the same or thicker in a plane parallel to the eye's optical axis than in a plane perpendicular to the eye's optical axis such that a compressive force sufficient to effect a 1.0 mm in diameter compression of said lens results in less than approximately 1.0 mm of axial displacement of said optic portion along the eye's optical axis.

2. An intraocular lens to be implanted within an eye generally perpendicular to the eye's optical axis comprising:
   an outer peripheral edge defining an optic portion,
   two, three or four looped haptic elements each of non-uniform cross-section, each of non-uniform thickness as measured between an anterior surface for facing the cornea of the eye and a posterior surface for facing the retina of the eye of said haptic element and each permanently connected to said outer peripheral edge by two or more attachment portions of greatest haptic element thickness measured from the anterior to the posterior surface and becoming increasingly thin moving outwardly in a direction away from the optic portion, and
   each haptic element having flexible central portions flexible in a plane perpendicular to said eye's optical axis, unitarily formed with said attachment portions opposite said outer peripheral edge and dimensioned be the same or thicker in a plane parallel to the eye's optical axis than in a plane perpendicular to the eye's optical axis such that a compressive force sufficient to effect a 1.0 mm in diameter compression of said lens results in less than approximately 0.5 mm of axial displacement of said optic portion along the eye's optical axis.

3. An intraocular lens to be implanted within an eye generally perpendicular to the eye's optical axis comprising:

an outer peripheral edge defining an optic portion, two, three or four looped haptic elements each of non-uniform cross-section, each of non-uniform thickness as measured between an anterior surface for facing the cornea of the eye and a posterior surface for facing the retina of the eye of said haptic element and each permanently connected to said outer peripheral edge by two or more attachment portions of greatest haptic element thickness measured from the anterior to the posterior surface and becoming increasingly thin moving outwardly in a direction away from the optic portion, and each haptic element having flexible central portions flexible in a plane perpendicular to said eye's optical axis, unitarily formed with said attachment portions opposite said outer peripheral edge and dimensioned be the same or thicker in a plane parallel to the eye's optical axis than in a plane perpendicular to the eye's optical axis such that a compressive force sufficient to effect a 1.0 mm in diameter compression of said lens results in less than approximately 0.3 mm of axial displacement of said optic portion along the eye's optical axis.

4. The intraocular lens of claim 1, 2 or 3 wherein the looped haptic elements and the optic portion are both formed of a foldable or compressible material.

5. The intraocular lens of claim 1, 2 or 3 wherein said lens is formed from one or more materials selected from the group consisting of silicone polymers, hydrocarbon polymers, fluorocarbon polymers, hydrogels, soft acrylic polymers, polyester, polyamides, polyurethane, silicone polymers with hydrophilic monomer units and fluorine-containing polysiloxane elastomers.

6. The intraocular lens of claim 1, 2 or 3 wherein said lens is formed from a hydrogel material.

7. The intraocular lens of claim 1, 2 or 3 wherein said lens is formed from a hydrogel material which is 18 percent by weight water.

8. The intraocular lens of claim 1, 2 or 3 wherein said lens is formed from poly(HEMA-co-HOHEXMA).

9. The intraocular lens of claim 1, 2 or 3 wherein said lens is formed from a material having a refractive index above 1.33.

10. The intraocular lens of claim 1, 2 or 3 wherein said lens is formed from an acrylic material.

11. The intraocular lens of claim 1, 2 or 3 wherein said lens is formed from a silicone material.

12. The intraocular lens of claim 1, 2 or 3 wherein said flexible central portions of said looped haptic elements are dimensioned to be the same or smaller in size in a plane generally perpendicular to the eye's optical axis, or width, than in a plane generally parallel to the eye's optical axis, or thickness.

13. The intraocular lens of claim 1, 2 or 3 wherein a glare reduction zone is formed adjacent to the outer peripheral edge of the optic portion.

14. The intraocular lens of claim 1, 2 or 3 wherein one or more of said looped haptic elements includes a stiffening element having a greater resistance to bending in a plane generally parallel to an eye's optical axis than in a plane generally perpendicular to the eye's optical axis.

15. The intraocular lens of claim 1, 2 or 3 wherein the haptic element includes a stiffening element formed from a material selected from the group consisting of polyimide, polyolefin, high-density polyester, nylon and metal.

\* \* \* \* \*